(12) United States Patent
Quetel et al.

(10) Patent No.: US 11,964,069 B2
(45) Date of Patent: Apr. 23, 2024

(54) PROCESS AND DEVICE FOR STERILIZING GAS FILTRATION MEANS, IN PARTICULAR BLOWING AIR

(71) Applicant: SIDEL PARTICIPATIONS, Octeville-sur-Mer (FR)

(72) Inventors: François Quetel, Octeville-sur-mer (FR); Benjamin Yger, Octeville-sur-mer (FR); Sandy Letellier, Octeville-sur-mer (FR); Jeremy Marie, Octeville-sur-mer (FR)

(73) Assignee: SIDEL PARTICIPATIONS, Octeville-sur-Mer (FR)

( * ) Notice: Subject to any disclaimer, the term of this patent is extended or adjusted under 35 U.S.C. 154(b) by 1153 days.

(21) Appl. No.: 16/070,365

(22) PCT Filed: Jan. 16, 2017

(86) PCT No.: PCT/FR2017/050087
§ 371 (c)(1),
(2) Date: Jul. 16, 2018

(87) PCT Pub. No.: WO2017/121973
PCT Pub. Date: Jul. 20, 2017

(65) Prior Publication Data
US 2021/0038752 A1     Feb. 11, 2021

(30) Foreign Application Priority Data

Jan. 15, 2016 (FR) ........................ 1650326

(51) Int. Cl.
*A61L 2/20*      (2006.01)
*A61L 12/00*    (2006.01)
*A61L 101/02*  (2006.01)

(52) U.S. Cl.
CPC ............... *A61L 2/208* (2013.01); *A61L 12/00* (2013.01); *A61L 2101/02* (2020.08); *A61L 2202/11* (2013.01); *A61L 2202/13* (2013.01)

(58) Field of Classification Search
CPC ...... A61L 2/208; A61L 12/00; A61L 2101/02; A61L 2202/11; A61L 2202/13;
(Continued)

(56) References Cited

U.S. PATENT DOCUMENTS

| 4,734,268 A | 3/1988 | Redding et al. |
| 5,173,258 A * | 12/1992 | Childers ................... A61L 2/20 |
| | | 422/294 |

(Continued)

FOREIGN PATENT DOCUMENTS

| EP | 0 243 073 | 10/1987 |
| EP | 0 815 919 | 1/1998 |

(Continued)

OTHER PUBLICATIONS

International Search Report, PCT/FR2017/050087, dated Mar. 24, 2017.

(Continued)

*Primary Examiner* — Sean E Conley
*Assistant Examiner* — Brendan A Hensel

(57) ABSTRACT

Disclosed is a process and a device for sterilizing gas filtration unit, characterized in that the sterilization process includes at least: —an application step consisting in circulating, through the gas filtration unit, a gas mixture including hot air and a determined amount of hydrogen peroxide vapor, in which the determined amount of hydrogen peroxide vapor is obtained by sequentially injecting, with a given time interval (t) between two successive injections, a given dose of hydrogen peroxide in the liquid state into the hot air; and —a sterilization step consisting, during the time interval (Continued)

(t), in circulating hot air through the filtration unit in order to eliminate, by evaporation, all or some of the hydrogen peroxide deposited on the filtration unit during the application step.

7 Claims, 1 Drawing Sheet

(58) Field of Classification Search
CPC ......... A61L 2/24; A61L 2/06; B01D 46/0028; B01D 2279/65
See application file for complete search history.

(56) References Cited

U.S. PATENT DOCUMENTS

| | | | |
|---|---|---|---|
| 2009/0169421 A1* | 7/2009 | Nagatani | ................ A61L 2/208 422/4 |
| 2012/0020848 A1 | 1/2012 | Hill | |
| 2016/0175468 A1 | 6/2016 | Quagliarella et al. | |
| 2016/0184814 A1* | 6/2016 | Funazuka | ................ B25J 21/02 422/565 |
| 2016/0235877 A1* | 8/2016 | Ruley | ..................... A61L 2/208 |

FOREIGN PATENT DOCUMENTS

| | | | | |
|---|---|---|---|---|
| EP | 0815919 A2 * | 1/1998 | ......... | B01D 46/0028 |
| EP | 1283061 A1 | 2/2003 | | |
| EP | 3 034 151 | 6/2016 | | |
| JP | 2002102319 A | 4/2002 | | |
| WO | 9317726 A1 | 9/1993 | | |

OTHER PUBLICATIONS

EPO Notification, App. No. 17706532.3 dated Jul. 27, 2021.
JP Office Action, App. No. 2018-536755 dated Oct. 5, 2021.
English Translation, JP Office Action, App. No. 2018-536755 dated Oct. 5, 2021.

* cited by examiner

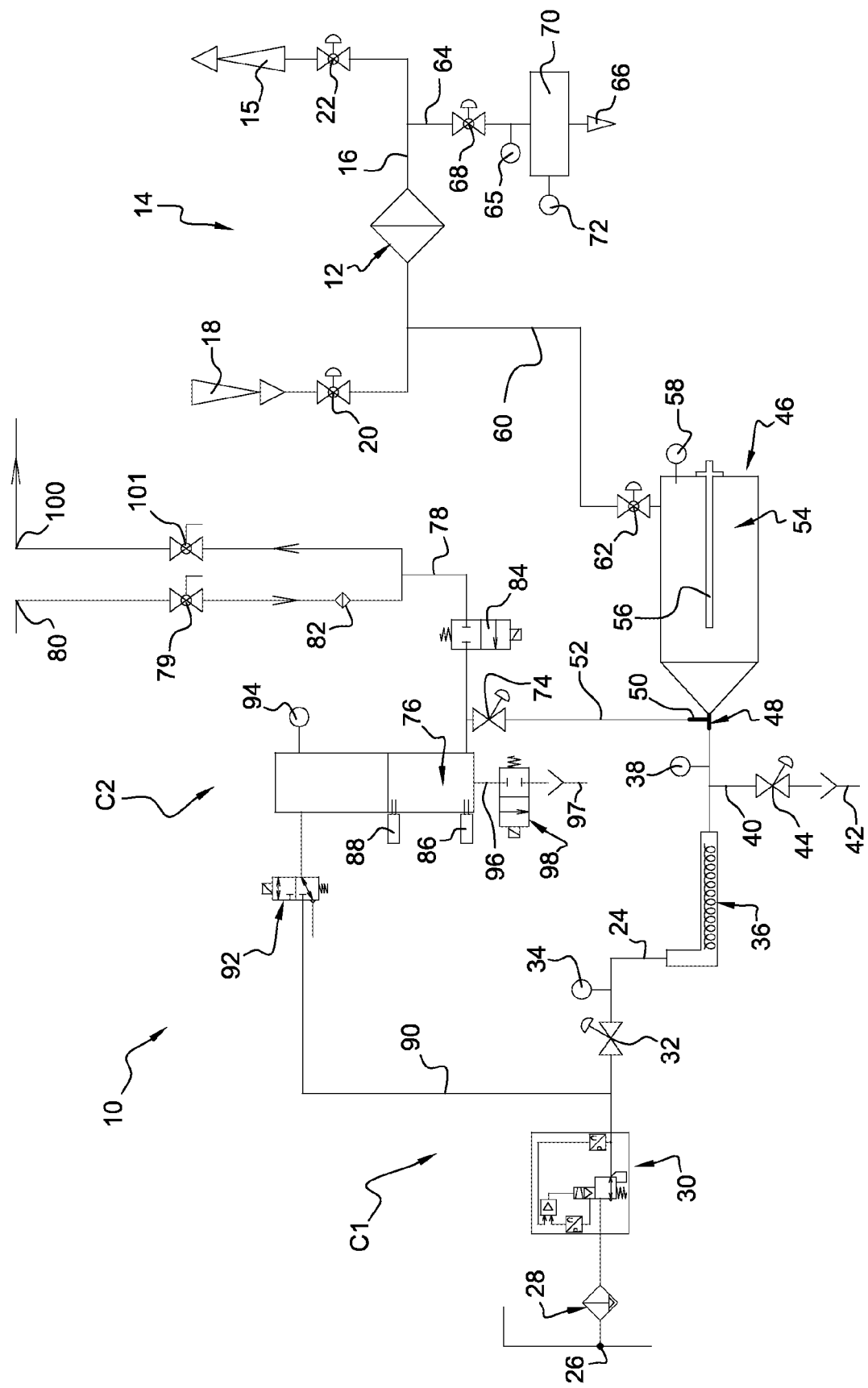

PROCESS AND DEVICE FOR STERILIZING GAS FILTRATION MEANS, IN PARTICULAR BLOWING AIR

CROSS-REFERENCE TO RELATED APPLICATION

The present application is a 35 U.S.C. 371 National Stage Entry of Patent Cooperation Treaty Patent Application No. PCT/FR2017/050087 filed on Jan. 16, 2017, which claims priority to French Patent Application No. 1650326 filed Jan. 15, 2016, the entire contents of which are hereby incorporated by reference.

TECHNICAL FIELD

This invention relates to a method and a device for sterilizing gas filtration means, in particular blowing air.

This invention relates more particularly to a method for sterilizing gas filtration means and a device for sterilizing gas filtration means according to said sterilization method.

BACKGROUND

The state of the art of numerous types of gas filtration means and most particularly of air filtration means is known.

Such gas filtration means are used in particular for the filtration of blowing air in installations for manufacturing containers made of thermoplastic material, with the manufacturing of containers made of thermoplastic material being achieved by blow molding (or by stretch blow molding) in a mold of hot preforms by means of at least one pressurized fluid.

The containers, such as bottles, flasks or jars, are generally obtained from preforms that are manufactured in advance by injection molding of thermoplastic material, such as PET (PolyEthylene Terephthalate), and that are subsequently conditioned thermally to obtain hot preforms that can allow molding.

To do this, an installation comprises at least one furnace for the thermal conditioning of preforms combined with a molding machine (or "blower") for the molding of containers from said hot preforms. The installation also advantageously comprises a sterilization unit for sterilizing at least the interior of preforms in such a way as to obtain so-called "sterile" containers.

To carry out the molding by blow molding or by stretch blow molding a hot preform, it is known to use for the blow molding at least one fluid, generally a gas, such as air that is compressed at pressures that can reach values of 30 or 40 bar according to the applications.

The air that is used for blow molding is introduced via the opening (the neck) of the hot preform that is placed in a mold, in such a way that the blowing air enters directly into contact with the inner surface of the container.

However, the inner surface is itself designed to be subsequently in contact with the contents of the container.

The quality of the blowing air, more particularly the absence of contaminants, such as microorganisms, particles such as dust, etc., is therefore an important parameter to take into account so as to be able to ensure in the case of food packaging good preservation of the packaged product, in particular a preservation period, and the safety of the consumer.

However, the quality of the compressed air that is used for the blow molding is determined by a set of factors, from the quality of the atmospheric air that is drawn in and that varies depending on the environment of the industrial site and its location in relation to pollution sources to the state of the distribution network and/or of the installation.

The atmospheric air that is drawn in and compressed by at least one compressor has, for example, a more or less large degree of hygrometry where humidity promotes corrosion and the development of microorganisms.

Particular attention is also paid to the selection of compressors that, in particular because of the design of their lubricating means, are likely to produce chemical contamination of air, for example with lubricating oil or else Teflon dust.

This is the reason for which the compressed air, intended to be used for blow molding, is treated in advance and most particularly filtered by gas filtration means so as to obtain a blowing air that is "sterile," i.e., in particular free of microorganisms.

The compressed air that is used for blow molding is generally successively filtered by a filtration system that comprises various gas filtration means.

In a non-limiting manner, such an air filtration system that is intended for blow molding comprises, for example, multiple filtration means that, arranged in series, are intended to deliver sterile air at the output.

The air is successively filtered there by, for example, first "FFP"-type filtration means to achieve in particular de-oiling, water purification, and elimination of dust, and then the second "AK"-type filtration means (with activated carbon) for removing all of the oil and gaseous hydrocarbon vapors, which can also cause odor and taste contamination, and finally by third "SRF"-type filtration means to retain the microorganisms.

Actually, the blowing air is likely to be a vector for contamination of the interior of the preform and therefore of the container, by introducing therein contaminants and most particularly microorganisms (viruses, germs, spores, etc.).

Controlling the quality of the compressed air used for blow molding is even more important when, in the container manufacturing method, the filling of containers is carried out in an aseptic environment immediately after the molding of the container that is obtained by blow molding or by stretch blow molding of a hot preform.

Actually, in such a manufacturing method, the sterilization is generally carried out upstream on the preforms, before their transformation into containers, in such a way that it is then essential to prevent the risks of contamination of sterilized preforms, such as that of containers that are manufactured from these preforms.

The purpose of the invention is to sterilize the gas filtration means, in particular but not exclusively blowing-air filtration means, such as, for example, the "SRF"-type filtration means that are used to eliminate the microorganisms from the compressed air intended for blow molding for the manufacturing of sterile containers.

Solutions are sought for sterilizing such gas filtration means before a first use just as after a certain use.

The sterilization of the filtration means is to make it possible to destroy the microorganisms that are present, resulting in particular from the use of said filtration means, so as to prevent their development in the filtration means and thus to eliminate the risks of such microorganisms migrating downstream from said filtration means during use.

In the case of an industrial application such as that of the manufacturing of containers designed for the packaging of food products, it is important to be able to ensure a quality and most particularly the sterility of the blowing air that is filtered using such gas filtration means.

With such sterilization, it is sought for economic reasons also to reduce the frequency of changing the filtration means.

To sterilize the gas filtration means (or filters), it is known from the state of the art to use water vapor, in particular for sterilizing filters designed to filter air at low pressure.

Such a sterilization with water vapor has also been used, however, to sterilize gas filtration means intended for the filtration of blowing air, such as filters provided for operating at high pressure such as the above-mentioned FFP-type filters.

The sterilization is then generally carried out with a water vapor of food quality, i.e., a vapor that is characterized by a very low water content and the absence of impurities.

Such a sterilization with water vapor of the filtration means used for filtering the blowing air in an installation for manufacturing containers made of thermoplastic material has not, however, been satisfactory for the reasons presented in detail below.

First of all, it was possible to note that the quality of the water vapor used during sterilization was disparate. Generally of an inadequate, sometimes mediocre quality, the quality of the water vapor proves mainly heterogeneous from one industrial site to another for the same installation for manufacturing containers.

Then and even with quality water vapor, the sterilization of the filtration means obtained is not satisfactory.

Under these conditions and to preserve the filtration quality, it thus is not rare to note an increase in the frequency of sterilization of the filtration means and also a noticeable reduction of their service life.

However, the sterilization of the filtration means (like changing thereof) requires an interruption of use, or, in our example of use, a halt in the manufacturing of containers, which is particularly harmful economically.

Studies have made it possible to note the presence of excess water in the filtration means after such operations of sterilization by vapor.

It was also possible to establish that the temperatures induced by the use of water vapor, higher than 120° C., caused damage to the filtration means and in so doing degraded the filtration properties thereof for subsequent use.

In addition to the absence of homogeneity in the quality of the water vapor used for sterilization, it was possible to note in particular that an accumulation of water condensates occurred in the thus sterilized filtration means, with these condensates remaining trapped in the filtration means and proving particularly difficult to eliminate.

In a sterilization with water vapor, air compressed at ambient temperature is used to eliminate water so as to dry the filtration means. Such drying requires a large amount of air since the flow rates implemented are, for example, on the order of 2,000 to 3,000 m³/h.

The air pressure used for drying should not exceed certain pressure values, for example 4 bar, for fear of causing deterioration of the structure of the filtration means.

Actually, the presence of water in the filtration means opposes the passage of the drying air through the filtration means and, by clogging them, the water modifies the pressure drop thereof.

Finally, the drying air tends to push by force the condensates through the filtration means, whereas the gas filtration means are hydrophobic.

Consequently, the sterilization with water vapor causes a degradation of the filtration means that can go so far as to their destruction, destruction that further exhibits a totally unpredictable nature.

It results from the foregoing that the performances of the filtration means of the blowing air thus sterilized with water vapor degrade and that their service life is considerably reduced.

In addition, an imperfect elimination of the water condensates after sterilization with water vapor of the filtration means may prove particularly harmful then during the resumption of their use.

Actually, the water condensates that are still present in the filtration means (because of excess water and the difficulty of its elimination) will then be pushed downstream by gas such as blowing air.

In the case of an installation for manufacturing containers, the blowing air under high pressure pushes the water residues downstream from the filtration means, i.e., in the blow-molding circuit and then in the manufactured containers themselves, with the consequence of wetting the blow-molding circuit and primarily introducing humidity inside the manufactured containers.

However, the presence of humidity inside manufactured containers increases the risks of microbiological contamination.

Furthermore, there is an operating mode for sterilizing the filters other than the use of the vapor as described above; this is sterilization by chemical means, i.e., in particular the use of hydrogen peroxide for sterilizing the filters.

The documents EP0815919, US2009/169421, EP0243073 describe sterilization by chemical means by impregnating—a single time—hydrogen peroxide filters either in the liquid state or in the gaseous state and by activating hydrogen peroxide by hot air.

SUMMARY

The purpose of this invention is in particular to resolve the above-mentioned drawbacks and most particularly to propose a new approach for sterilizing gas filtration means, such as the means for filtering the blowing air that are used in an installation for manufacturing containers made of thermoplastic material.

For this purpose, the invention proposes a method for sterilizing gas filtration means, characterized in that said sterilization method comprises at least:
 An application step consisting in circulating through the gas filtration means a gaseous mixture that comprises hot air and a specified amount of hydrogen peroxide vapor, in which said specified amount of hydrogen peroxide vapor is obtained by injecting sequentially, with a given time interval (t) between two successive injections, a given dose of hydrogen peroxide in the liquid state in hot air; and
 A sterilization step consisting, during said time interval (t), in circulating hot air through said filtration means to eliminate by evaporation all or part of the hydrogen peroxide that is deposited on said filtration means during said application step.

Advantageously, the sterilization method according to the invention makes it possible to sterilize effectively the gas filtration means, while preserving their integrity in such a way as to maintain its filtration performances and to increase its service life, at the very least to preserve it.

Actually, the risks of degradation, and even destruction, of the structure of the filtration means are eliminated with a chemical sterilization according to the invention.

By comparison with the sterilization by water vapor, the invention does not require a large amount of air because the hydrogen peroxide condensates are successively eliminated by heating by means of hot air.

The sterilization according to the invention is more economical in air with a flow rate of hot air that is more than 100 times less than that of the air used for drying in the method for sterilization with water vapor or for the evaporation of the injected hydrogen peroxide that is continuous according to the state of the art.

Advantageously, the sterilizing mixture comprises a specified dose of hydrogen peroxide in the vapor state that is deposited by condensation on the filtration means when the gaseous mixture of hot air and vapor enters into contact with the filtration means.

Advantageously, the hydrogen peroxide condensates are then eliminated gradually by evaporation owing to the heating with hot air, with said evaporation being carried out at least between the injection of two successive doses of liquid hydrogen peroxide.

According to an important characteristic, it should be well understood that the sterilization method according to the invention is a method of a "chemical" nature.

Actually, and by comparison with sterilization by water vapor, the sterilizing effect does not result (or not only) from a thermal destruction of the microorganisms that are present in the filtration means, by the provision of heat due to water vapor.

In the invention, the hot air has two purposes: that of thermally activating the condensed hydrogen peroxide on the filtration means and that of eliminating from it, according to the application period of the hot air, at least a portion by evaporation.

The hot air will first bring about a gradual elimination by evaporation of the water that is present in the hydrogen peroxide condensates, which will have the effect of gradually increasing its concentration and therefore increasing its sterilizing effect.

In the case of a sterilizing agent that is formed by hydrogen peroxide ($H_2O_2$), thermal activation refers to the fact that the hot air acts on hydrogen peroxide to break its chemical bonds, which brings about the appearance of active free radicals (OH) that will destroy the microorganisms and will make it possible to obtain the desired degree of sterilization.

The sterilizing agent that is used for the sterilization of the filtration means according to the invention is advantageously hydrogen peroxide ($H_2O_2$), known for its germicidal properties, in particular in the food domain.

When the hydrogen peroxide is also used in the installation for manufacturing containers to sterilize at least the interior of the preforms made of thermoplastic material, the supply source of hydrogen peroxide is, for example, able to be a common source with the devices for sterilizing the filtration means of blowing air, on the one hand, and preforms, on the other hand.

Advantageously, the method for sterilizing filtration means according to the invention comprises by turns, i.e., alternately, at least one step for application of the gaseous mixture that comprises the hydrogen peroxide vapor obtained from said specified dose and a sterilization step that uses hot air.

Said application and sterilization steps respectively constitute a sequence that is advantageously repeated "n" number of times for carrying out a sterilization cycle, with the evaporation of the hydrogen peroxide condensates being carried out at least in the time interval given between two successive injections of a specified dose of hydrogen peroxide.

After the repetition "n" times of said sequence, the sterilization method advantageously comprises, at the end of the cycle, an additional sterilization step that consists, as during said given time interval, in circulating only hot air through said filtration means to accomplish, if necessary, the elimination of hydrogen peroxide by evaporation.

The additional sterilization step is carried out during a period that is specified in particular based on the value of said time interval, with said step being able to be eliminated when said time interval is sufficient for ensuring a total evaporation of the hydrogen peroxide condensates deposited after the injection of each specified dose.

The sequential injection of hydrogen peroxide, i.e., the alternating repetition of said application steps of a fraction of the specified amount of vapor and then hot air for the sterilization, advantageously makes it possible not to saturate the filtration means, in particular preventing any clogging.

Owing to the sequential injection of a given dose of hydrogen peroxide, a minimum amount of hydrogen peroxide is deposited, which can then be totally or at least partially eliminated by hot air during said given time interval and this before initiating a new application resulting from the injection of a new given dose.

Advantageously, the sequential injection makes it possible to reduce the amount of energy that is necessary for sterilizing and to preserve the means for filtering degradations in particular as a result of temperature effects.

The total amount of hot air (and therefore of energy) that is necessary to the evaporation of all of the hydrogen peroxide is smaller when said hydrogen peroxide is applied intermittently than if the amount corresponding to the sum of the doses was applied a single time.

Advantageously, the temperature of the hot air that is required for evaporating the equivalent of a specified dose is also lower so that it participates in preserving the means for filtering degradations, such as those previously observed by comparison with the water vapor.

After its evaporation, the hydrogen peroxide in the gaseous state is free to pass through the filtration means completely, to penetrate in depth into the interior but without ever altering the structure thereof as the water vapor condensates were doing.

For an equal amount of hydrogen peroxide vapor, the sterilization obtained from the filtration means is better accomplished by successively carrying out the sequence of said application and sterilization steps "n" times than by projecting an equivalent amount of hydrogen peroxide vapor a single time.

According to other characteristics of the sterilization method according to the invention:

The method comprises at least one vaporization step that consists in vaporizing said given dose of hydrogen peroxide in the liquid state in evaporation means for obtaining said gaseous mixture that is used during the application step;

The method comprises at least one injection step that consists in sequentially injecting, with said given time interval between two successive injections, said given dose of hydrogen peroxide in the liquid state in a continuous stream of hot air and in introducing the entire dose into said evaporation means to obtain said gaseous mixture;

The step for injecting said given dose of hydrogen peroxide is carried out sequentially by selectively controlling regulating means, respectively in the open position during a given time lapse and in the closed position during a given time interval between two successive injections of said given dose of hydrogen peroxide in the liquid state;

The sterilization method consists in carrying out at least one cycle during which a sequence, comprising said application and sterilization steps, is repeated "n" number of times;

The method comprises at least one additional sterilization step that consists in circulating only hot air through said filtration means for a period that is determined based on the time interval to ensure evaporation of hydrogen peroxide.

The invention also proposes a sterilization device that comprises at least a first circuit that comprises at least air heating means that can deliver hot air at a specified target temperature, a second circuit that comprises at least regulating means that are controlled to inject hydrogen peroxide selectively, and at least one evaporator to prepare a gaseous mixture that consists of hot air and hydrogen peroxide vapor.

According to other characteristics of the sterilization device according to the invention:

The second circuit comprises at least one reservoir with a specified capacity that is designed to be filled with hydrogen peroxide in the liquid state;

The device comprises at least one pipe that selectively connects the evaporator to a pipe that comprises said filtration means;

The device comprises a control unit for selectively controlling regulating means of the first circuit and/or of the second circuit between at least one open position and one closed position.

Other characteristics and advantages of the invention will become clear from reading the following description, for the understanding of which reference will be made to the single figure that diagrammatically shows an embodiment of a sterilization device that is designed to be integrated in a container manufacturing installation to sterilize the gas filtration means thereof.

BRIEF DESCRIPTION OF THE DRAWINGS

FIG. 1 shows a pneumatic diagram illustrating an embodiment of a sterilization device 10 for sterilizing gas filtration means 12 according to example embodiments of the present invention.

DETAILED DESCRIPTION

In the embodiment, said gas filtration means 12 consist of blowing-air filtration means.

The filtration means 12 are designed to filter high-pressure compressed air to deliver sterile air that can be used as a blow-molding fluid in an installation (not shown) for manufacturing containers made of thermoplastic material from hot preforms.

The high-pressure compressed air that is used for the blow molding of hot preforms to form containers, below referred to as the blowing air, is to be "sterile" air, i.e., free of contaminants and most particularly of microorganisms.

"High pressure" refers in a general manner both to the final pressure of the blowing air, which can reach 25 or 40 bar for certain applications, and to a lower pressure that is intended for pre-blow molding or also for blow molding, and between, for example, 7 and 20 bar.

According to the invention, chemical sterilization of the air filtration means 12 is initiated by using at least one sterilizing agent in the vapor state that, after having been deposited on said filtration means 12, is activated thermally and eliminated by evaporation by means of hot air produced by the sterilization device 10.

The sterilizing agent that is used for the sterilization of the filtration means is hydrogen peroxide ($H_2O_2$).

In the embodiment illustrated in the figure, the filtration means 12 comprise at least one filter.

In a variant, not shown, the filtration means 12 comprise more than one filter to filter the air that is intended for blow molding.

To deliver sterile air, the filtration means 12 consist of, for example, at least one "SRF"-type filter.

Preferably, said filtration means 12 shown in the figure form the multiple last filtration means of a filtration system of the type described above and are in particular able to carry out a final filtration of the air before its use for blow molding.

Preferably, said multiple filtration system comprises means for dehumidifying air.

Such filtration means 12 are more particularly intended to eliminate the microorganisms from air and can, to do this, comprise more than one filtration stage.

In a variant, not shown, the filtration means 12 comprise at least two filtration stages, for example in a series, to carry out a double filtration. Independently of the number of filtration stages, one filtration stage can also comprise more than one filtration means (or filter), for example two filters in parallel.

Only a part of a blow-molding circuit 14 of a molding machine or "blower" (not shown) was shown in the figure.

In a known manner, such a molding machine is, for example, of the rotary type and is provided with a number of stations for the forming by blow molding or by stretch blow molding of the containers made of thermoplastic material from hot preforms.

The filtration means 12 are arranged in a main pipe 16. The pipe 16 is connected at one end, upstream from the filtration means 12, to a blowing air source 18 that delivers said compressed air under pressure and whose maximum value is determined based on applications.

Regulating means 20 are arranged in the pipe 16 between said blowing air source 18 and the filtration means 12, to be able in particular to isolate said filtration means 12 during the sterilization by means of said sterilization device 10.

In the open position, the regulating means 20 allow, from the blowing air source 18 that is located upstream, a circulation of air from upstream to downstream in the pipe 16 and, in the closed position, the regulating means 20 interrupt said air circulation in the pipe 16, between the blowing air source 18 and the filtration means 12 that are located downstream.

The pipe 16 is connected at the other end, downstream from the filtration means 12, to at least one part 15 of the blow-molding circuit 14 by which the blowing air that is filtered by said filtration means 12 is directed to the blow-molding means (not shown), such as at least one nozzle, combined with a mold of said container molding machine.

Regulating means 22 are arranged in the pipe 16 between said part 15 of the blow-molding circuit 14 and the filtration means 12, in particular for being able to isolate said filtration means 12 during the sterilization and in relation to said part 15 of the blow-molding circuit 14.

Preferably, the regulating means 20 and 22 are formed by at least one valve such as a solenoid valve.

The regulating means 20 and 22 are controlled selectively by a control unit (not shown) between at least one open position and one closed position.

In the open position, the regulating means 22 allow a circulation of air from upstream to downstream in the pipe 16 and, in the closed position, the regulating means 22 interrupt said air circulation in the pipe 16, between the filtration means 12 and the part 15 of the blow-molding circuit 14 that is located downstream.

Advantageously, the sterilization device 10 is controlled selectively between a sleep state in which said sterilization device 10 is inactive and a state of use in which the sterilization device 10 is active, used for sterilizing the filtration means 12.

Preferably, and according to the embodiment, the sterilization device 10 equips an installation for manufacturing containers made of thermoplastic material by blow molding or by stretch blow molding of the hot preforms.

Advantageously, the sterilization device 10 can equip a manufacturing installation, whether said installation is new or existing.

As a variant, the sterilization device 10 constitutes an independent unit of the installation that can sterilize various gas filtration means.

The sterilization device 10 is more particularly combined with the blow-molding machine (or blower) of such an installation for sterilizing the air filtration means 12 thereof.

The sterilization device 10 of the air filtration means according to the invention is able in particular to replace a water vapor sterilization device there according to the state of the art and as described in the preamble.

Preferably, the sterilization device 10 is able to sterilize blowing-air filtration means 12 in place, i.e., in the position of use that said filtration means 12 occupy when containers are manufactured by the installation and when the inactive sterilization device 10 is in in the sleep state.

Advantageously, no intervention is required on the filtration means 12, in particular no human intervention to initiate disassembly and reassembly.

The sterilization is consequently able to be carried out automatically by controlling the sterilization device 10.

To carry out such a sterilization of the blowing-air filtration means 12 by means of the sterilization device 10, the manufacturing of containers is to be interrupted in advance.

A change in the operating mode of the installation is initiated initially by switching from an operating mode for manufacturing containers, in which containers are able to be manufactured from hot preforms, to another operating mode, a so-called intervention mode, in which the manufacturing of containers stops.

Interventions such as the sterilization of the blowing-air filtration means 12 by means of the sterilization device 10 are then able in particular to be carried out.

The change in operating mode of the installation for the purpose of initiating a sterilization of the blowing-air filtration means 12 is accompanied by a change of state of the sterilization device 10 that is activated, switching from the sleep state to the state of use.

Below, the device 10 for sterilizing filtration means will be described according to the embodiment that is illustrated in the figure and whose operation will be described in detail subsequently.

In the embodiment that is illustrated in the figure, the sterilization device 10 comprises at least a first circuit C1 primarily for the air that is associated with a second circuit C2 for the sterilizing agent that is formed here by hydrogen peroxide ($H_2O_2$).

The sterilization device 10 is designed in particular for the implementation of the method for sterilizing gas filtration means according to the invention.

The sterilization device 10 is designed in particular to be used for the sterilization of blowing-air filtration means in an installation for manufacturing containers made of thermoplastic material from hot preforms.

According to the invention, the method for sterilizing gas filtration means comprises at least:

An application step that consists in circulating through the gas filtration means a gaseous mixture that comprises hot air and a specified amount of hydrogen peroxide vapor, in which said specified amount of hydrogen peroxide vapor is obtained prior to the application by sequentially injecting, with a given time interval (t) between two successive injections, a given dose of hydrogen peroxide in the liquid state; and A sterilization step that consists, during said time interval (t), in circulating hot air through said filtration means to eliminate by evaporation all or part of the hydrogen peroxide that is deposited on said filtration means during said application step. The first circuit C1 of the sterilization device 10 comprises at least one pipe 24 whose upstream end is connected to a compressed-air supply source 26.

Preferably, the compressed-air supply source 26 is a compressed-air distribution network that delivers air at a specified pressure, for example a low pressure of approximately 7 bar.

Advantageously, the first circuit C1 comprises compressed-air filtration means 28 delivered by said supply source 26.

Preferably, the filtration means 28 make it possible to eliminate the contaminants that are present in the compressed air and are arranged in the pipe 24 at the input of the first circuit C1, at the upstream end connected to the supply source 26.

Advantageously, the first circuit C1 comprises pressure-regulating means 30 so as to regulate the pressure of the compressed air that circulates in the pipe 24 to ensure a constant flow rate.

The pressure-regulating means 30 consist of, for example, a membrane pressure regulator that regulates the dynamic pressure of the compressed air.

Preferably, the pressure-regulating means 30 are arranged in the pipe 24, downstream from the means 28 for filtering the compressed air.

Advantageously, the first circuit C1 comprises means 32 for regulating the air circulation in the pipe 24. Preferably, the regulating means 32 are formed by at least one valve such as a solenoid valve.

The regulating means 32 are arranged in the pipe 24, for example downstream from the pressure-regulating means 30, and are controlled to establish selectively a compressed air circulation in the pipe 24.

The regulating means 32 are controlled selectively by a control unit (not shown) between at least one open position and one closed position.

Preferably, the sterilization device 10 comprises a control unit for controlling in particular all of the regulating means.

In the open position, the regulating means 32 allow a circulation of compressed air from upstream to downstream in the pipe 24 and, in the closed position, the regulating means 32 interrupt said air circulation in the pipe 24.

Preferably, the first circuit C1 comprises pressure-measuring means 34 arranged to measure the pressure of the compressed air that circulates in said pipe 24.

Advantageously, the first circuit C1 comprises heating means 36 for heating the compressed air that is selectively put into circulation in the pipe 24.

The pressure-measuring means 34 are preferably arranged downstream from the regulating means 32 and upstream from the heating means 36.

The pressure-measuring means 34 are formed by, for example, a pressure probe, making it possible in particular to monitor the dynamic pressure of the air in circulation in the pipe 24 of the first circuit C1.

The heating means 36 comprise, for example, at least an air heater that is able to heat the compressed air that circulates in the pipe 24 to a given target temperature (Tc).

The means 36 for heating air are controlled selectively so that the temperature of the air that circulates downstream is at least at said target temperature (Tc).

Preferably, the given target temperature (Tc) is a temperature on the order of 220° C. Such a target temperature value (Tc) makes it possible to obtain hot air that has a temperature of approximately 110° C. when it comes into contact with said filtration means 12.

Such a temperature of the hot air, advantageously less than 120° C., makes it possible not to deteriorate the filtration means 12 when the hot air comes into contact with them.

To control the heating means 36 selectively and to monitor the temperature of the hot air, the circuit C1 of the sterilization device 10 comprises temperature-measuring means 38.

The temperature-measuring means 38 are able to measure the temperature of the hot air that circulates in the pipe 24 after having passed through the heating means 36 that are formed by said at least one heater.

Preferably, the means 38 for measuring the temperature of the air are arranged downstream from said heating means 36.

The circuit C1 of the sterilization device 10 comprises a purge pipe 40 whose upstream end is connected to the pipe 24 and whose other downstream end is connected to means 42 for discharging outside of the sterilization device 10.

The discharge means 42 are designed to collect air, hot or not, in particular when the temperature of the air is not in accordance with said target temperature (Tc).

Preferably, the purge pipe 40 is connected to the pipe 24 downstream from the means 36 for heating the air.

Regulating means 44 are arranged in the purge pipe 40 and are controlled to establish selectively a circulation of air in the pipe 40, in the bypass of the pipe 24.

Preferably, the regulating means 44 are formed by at least one solenoid valve.

The regulating means 44 are controlled selectively by said control unit (not shown) between at least one open position and one closed position.

In the open position, the regulating means 44 allow a circulation of compressed air from upstream to downstream in the purge pipe 40, and, in the closed position, the regulating means 44 interrupt said air circulation in the purge pipe 40.

The pipe 24 of the first circuit C1 comprises, at another end, at least one evaporator 46 downstream or opposite to the compressed-air supply source 26.

Preferably, a connection 48 is inserted between the pipe 24 and an inlet of said at least one evaporator 46.

The connection 48, for example in the shape of an inverted "T," comprises an inner main pipe into which means 50 for injecting hydrogen peroxide empty.

Advantageously, the means 50 for injecting the sterilizing agent that is formed by hydrogen peroxide are able to spray it in the form of a mist formed by very fine droplets.

A pipe 52 for injecting hydrogen peroxide from the second circuit C2 of the sterilization device 10 is connected to said injection means 50 that empty into the pipe of the connection 48 to inject, into the hot air that passes through it, the hydrogen peroxide in the liquid state.

The evaporator 46 comprises a cavity 54 inside of which are arranged at least heating means 56 for producing the sterilizing agent vapor from the mixture of hot air obtained from the pipe 24 of the first circuit C1 and the hydrogen peroxide in the liquid state that is obtained from the injection pipe 52 of the second circuit C2.

Temperature-measuring means 58 are combined with the evaporator 46 to measure the temperature of the mixture that is present inside the cavity 54 and that consists of hot air and hydrogen peroxide vapor, which is advantageously introduced sequentially by doses in the area of the connection 48.

The evaporator 46 is connected to the pipe 16 of the blow-molding circuit 14 by a pipe 60. An upstream end of the pipe 60 communicates with the cavity 54 of the evaporator 46, and the other downstream end of the pipe 60 connects to the pipe 16.

The pipe 60 of the sterilization device 10 connects to the pipe 16 between the regulating means 20 and the filtration means 12.

Regulating means 62 are arranged in the pipe 60 to control selectively the circulation in said pipe 60 of the gaseous mixture that, consisting of hot air and hydrogen peroxide vapor produced by the evaporator 46, is designed to be introduced into the blow-molding circuit 14 and more specifically into the pipe 16 for the sterilization of said filtration means 12.

Preferably, the regulating means 62 are formed by at least one valve such as a solenoid valve. The regulating means 62 are controlled selectively by the control unit (not shown) between at least one open position that allows the circulation of the mixture in the pipe 60 and one closed position that interrupts the circulation in the pipe 60.

The temperature-measuring means 58 are used in particular to control at least the heating means 56 and/or the regulating means 62.

A discharge pipe 64 is provided for discharging toward the collecting means 66, such as a sewer, effluents from the mixture after the sterilization of the filtration means 12.

The discharge pipe 64 comprises an end that is connected to the pipe 16 between the filtration means 12 and the regulating means 22, and another end that communicates downstream with said collecting means 66.

Regulating means 68, such as a solenoid valve, are arranged in the discharge pipe 64 to control the circulation in said pipe 64.

The regulating means 68 are controlled selectively by the control unit (not shown) between at least one open position that allows the circulation in the discharge pipe 64 and a closed position that interrupts the circulation in said pipe 64.

A part of the mixture that is introduced into the pipe 16 by means of the pipe 60 is, after having sterilized the filtration means 12, discharged via the discharge pipe 64 toward the collecting means 66 when the regulating means 68 are in the open position.

Temperature-measuring means 65 are arranged to measure the temperature in the discharge pipe 64.

Preferably, the temperature-measuring means 65 consist of a thermocouple.

Advantageously, the first temperature-measuring means 65 make it possible to carry out monitoring of the temperature during the sterilization of the filtration means 12 and to return the measurement to the control unit.

Preferably, treatment means 70 are inserted into the discharge pipe 64, upstream from the collecting means 66.

Such treatment means 70 comprise, for example, water and are designed in particular for treating the hydrogen peroxide that is present in the gaseous state in the effluents that circulate in the discharge pipe 64.

Means 72 for measuring the hydrogen peroxide concentration are advantageously combined with the treatment means 70 so as to carry out monitoring, in particular before discharging toward the collecting means 66.

The means 72 for measuring the hydrogen peroxide concentration are advantageously used to check, at the end of the sterilization cycle, to make sure that the amount of hydrogen peroxide that is measured is smaller than a threshold value that means that all of the hydrogen peroxide has been duly evaporated.

The second circuit C2 of the sterilization device 10 is designed to deliver the hydrogen peroxide that is used for sterilizing the filtration means 12.

The pipe 52 for injecting hydrogen peroxide that is connected, via the connection 48 and the injection means 50, to the first circuit C1 of hot air of the sterilization device 10 comprises regulating means 74.

The regulating means 74, such as a solenoid valve, are arranged in the injection pipe 52 and are controlled selectively by the control unit (not shown) between at least one open position that allows the circulation in the pipe 52 and a closed position that interrupts the circulation in the pipe 52.

The expression "specified amount" of hydrogen peroxide means the amount of hydrogen peroxide that is necessary to sterilize the filtration means for a sterilization cycle.

Furthermore, the expression "given dose" and "specified dose" is understood as being a fraction of the specified amount of hydrogen peroxide that is necessary for carrying out a filter sterilization cycle.

Consequently, the given dose sum corresponds to the specified amount of hydrogen peroxide that is necessary for carrying out a filtration means sterilization cycle.

The second circuit C2 comprises at least one reservoir 76 that has a specified capacity. The reservoir 76 is designed to be filled with a specified amount of hydrogen peroxide in the liquid state.

Preferably, the reservoir 76 is connected by a supply pipe 78 to a hydrogen peroxide supply source 80. The hydrogen peroxide has, for example, a concentration on the order of 25%.

Preferably, the pipe 78 comprises at least one valve 79 to be able to isolate the pipe 78 and therefore the second circuit C2 from the source 80 in such a way as to make possible in particular maintenance interventions.

Advantageously, the pipe 78 comprises filtration means 82 to filter hydrogen peroxide upstream from the reservoir 76.

The second circuit C2 comprises regulating means 84 that are arranged in the supply pipe 78 to control the circulation of hydrogen peroxide in said pipe 78, between the source 80 and the reservoir 76.

Preferably, the regulating means 84 are arranged downstream from the filtration means 82 and upstream from the reservoir 76, more specifically upstream from the connection of the injection pipe 52 to the pipe 78.

The regulating means 84 are formed by, for example, a solenoid valve, such as a 2/2-type solenoid valve.

The regulating means 84 are controlled selectively by the control unit (not shown) between at least one open position that allows the circulation in the pipe 78 and a closed position that interrupts the circulation in the pipe 78.

With the regulating means 84 occupying the open position (as well as the valve 79), the hydrogen peroxide in the liquid state flows from the source 80 to the reservoir 76 by advantageously being filtered by the filtration means 82.

The reservoir 76 has a specified capacity that corresponds to, for example, the amount of hydrogen peroxide that is necessary for carrying out a sterilization cycle that makes it possible to sterilize the filtration means 12.

Of course, the capacity of the reservoir 76 can vary based on applications but could also be larger and not correspond to the amount that is necessary for implementing a single sterilization cycle.

The second circuit C2 comprises level-measuring means 86, 88, such as probes, for controlling the filling of the reservoir 76 or else the purging.

The level-measuring means comprise at least first measuring means 86 for measuring a low level in the reservoir 76 and second measuring means 88 for measuring a high level in the reservoir 76.

Advantageously, said measuring means 86 and 88 are connected to the control unit (not shown) to control in particular the closing of the regulating means 84 so as to interrupt the filling when the reservoir 76 contains the desired amount of hydrogen peroxide.

Advantageously, the reservoir 76 can be pressurized by means of a pipe 90 whose one end is connected upstream to the first circuit C1 of compressed air and whose other end downstream is connected to the reservoir 76.

Preferably, the pipe 90 is connected to the pipe 24 of the first circuit C1 downstream from the pressure-regulating means 30 and upstream from the regulating means 32.

Regulating means 92 are arranged in the pipe 90 for controlling the pressurization of the reservoir 76.

The regulating means 92 consist of, for example, a solenoid valve, such as a 3/2-type solenoid valve.

The regulating means 92 are controlled selectively by the control unit (not shown) between at least one open position that allows the circulation in the pipe 90 and a closed position that interrupts the circulation in the pipe 90.

In the open position of the regulating means 92, compressed air obtained from the first circuit C1 is allowed inside the reservoir 76 in such a way as to exert on the liquid hydrogen peroxide that is present in the reservoir 76 a pressure, for example on the order of 7 bar, or a pressure that is higher than the atmospheric pressure.

The pressurization ensures a good flow of the hydrogen peroxide outside of the reservoir 76, in particular toward the injection pipe 52.

The regulating means 92 ensure an air vent function that makes it possible to produce exposure to open air in particular during the filling of the reservoir 76 with sterilizing agent, with the pressurization of the reservoir 76 being carried out after its filling.

Preferably, the second circuit C2 of hydrogen peroxide comprises pressure-measuring means 94 combined with the reservoir 76 to measure in particular the pressure inside said reservoir 76 and its variations.

The pressure-measuring means 94 comprise, for example, at least one pressure sensor, connected to the control unit.

Advantageously, the pressure-measuring means 94 make it possible to monitor the pressure variation to determine the amount of hydrogen peroxide that is injected by means of the injection pipe 52.

The second circuit C2 of the sterilization device 10 comprises a purge pipe 96 whose upstream end is connected to the lower part of the reservoir 76 and whose other downstream end is connected to discharge means 97 outside of the sterilization device 10.

The discharge means 97 are designed to collect the sterilizing agent that consists of hydrogen peroxide in the liquid state.

Preferably, the purge pipe 96 is connected to the lower part of the reservoir 76.

Regulating means 98 are arranged in the purge pipe 96 and are controlled to establish selectively a circulation of hydrogen peroxide toward the discharge means 97.

Preferably, the regulating means 98 are formed by at least one solenoid valve. The regulating means 98 are controlled selectively by said control unit (not shown) between at least one open position and one closed position.

In the open position, the regulating means 98 allow a circulation of hydrogen peroxide in the purge pipe 96, from the reservoir 76 toward the discharge means 97.

In the closed position, the regulating means 98 interrupt the circulation of hydrogen peroxide in the purge pipe 96.

The second circuit C2 comprises a pipe 100 that is connected to the supply pipe 78, advantageously downstream from the filtration means 82.

The pipe 100 is intended to supply hydrogen peroxide in the liquid state to at least one other sterilization device that is used in the container manufacturing installation that comprises the sterilization device 10.

Preferably, the pipe 100 comprises at least one valve 101 to be able to interrupt the circulation of hydrogen peroxide in the pipe 100.

Advantageously, said other sterilization device is the one that is used for sterilizing at least the interior of the preforms for the manufacturing of containers made of thermoplastic material.

The use of the sterilization device 10 according to the embodiment that was just described and more particularly the implementation of the sterilization method according to the invention by means of such a sterilization device 10 will now be described.

As indicated above, for initiating the sterilization of filtration means 12 of the blowing air, the installation or at the very least the molding machine (or "blower") is regulated to interrupt the manufacturing of containers and to change the operating mode by switching from the container manufacturing operating mode to the intervention operating mode.

The sterilization device 10 is also regulated selectively to switch from the sleep state to the state of use so as to initiate the sterilization of the filtration means 12.

The sterilization device 10 is actually in the sleep state when the installation is in the container manufacturing operating mode.

The regulating means 20, 22 and 44 are then respectively in the open position, and the other regulating means of the sterilization device 10 are in the closed position.

Preferably, the method for sterilizing filtration means 12 comprises a preliminary phase that, beginning after the change in state of the sterilization device 10, consists in carrying out one or more preparatory steps before beginning the sterilization of the filtration means 12.

The preliminary phase comprises at least one step for isolating filtration means 12 so as in particular to be able to sterilize them.

The isolation step makes it possible to isolate the air filtration means 12 that are to be sterilized, in particular in relation to the blowing air circuit 14 located downstream from said filtration means 12.

Advantageously, the sterilization is carried out "on line" without disassembling the filtration means 12 and automatically owing to the sterilization device 10.

The isolation step consists in controlling some of the means 20, 22, 44 for regulating the sterilization device 10, when they consist of solenoid valves, from their open position to their closed position to isolate said filtration means 12.

To be able to obtain, on the one hand, the hot air that is used in the sterilization method and, on the other hand, the hydrogen peroxide vapor, the air heating means 36 that comprise at least said heater and the means 56 for heating the evaporator 46 are respectively supplied electrically, put under voltage.

The compressed air that is delivered by the source 26 is introduced into the first air circuit C1.

Advantageously, the air undergoes one or more treatment steps before being heated in particular by said heating means 36 of the first air circuit C1.

The air is heated by said heating means 36 during the preliminary phase until reaching a desired temperature, but it is also heated during the sterilization of the filtration means 12 according to the method.

Preferably, the method comprises at least one step for filtering the air that consists in filtering the air that is delivered by the compressed-air supply source 26.

In the sterilization device 10, the compressed air provided by the supply source 26, such as a low-pressure compressed-air distribution network that delivers air at a pressure on the order of 7 bar, is filtered by the filtration means 28.

Preferably, the method comprises at least one pressure-regulating step that consists in regulating in pressure the air that is delivered by said compressed-air supply source 26 to obtain a specified pressure in the first circuit C1 from said source 26, in such a way as to have a constant air flow rate.

Preferably, said pressure-regulating step is carried out after the step for filtering compressed air using the pressure-regulating means 30 of the first circuit C1 that is arranged downstream from the filtration means 28.

Advantageously, the method comprises at least one step for measuring the air pressure consisting in measuring the air pressure downstream from said pressure-regulating means 30 so as to control whether the air pressure is equal to said specified pressure.

Preferably, the preliminary phase of the method comprises a step for preheating the air that consists in heating the air that is delivered by the compressed-air supply source 26 until reaching at least a specified target temperature (Tc).

As indicated above, the air that is intended to be heated is advantageously filtered and/or pressure-regulated in advance.

The step for preheating the air also consists in heating the air in the cavity 54 of the evaporator 46 until reaching at least a specified target temperature (Tc).

The temperature of the air is advantageously measured by the measuring means 38 and by the measuring means 58 for determining if said air temperature is at least equal to said specified target temperature (Tc).

Preferably, the specified target temperature (Tc) is identical for the heating means 36 and the heating means 56.

By way of non-limiting example, the value of the target temperature (Tc) is approximately 220° C.

The method comprises at least one step for controlling the air temperature carried out at least during said preheating phase. The step for controlling the air temperature is advantageously continued subsequently during the entire sterilization method.

The step for controlling the air temperature consists in at least measuring the temperature of the heated air to control that the air temperature is at least equal to said target temperature (Tc).

In a sterilization device 10 according to the embodiment, said step for controlling the air temperature consists in measuring the temperature thereof by means of the temperature-measuring means 38 combined with the heating means 36 and/or the temperature-measuring means 58 combined with said heating means 56 of said at least one evaporator 46.

During the preheating step, the means 32, 62 and 68 for regulating the sterilization device 10 are in the open position, and the regulating means 44 are in the closed position.

The method comprises a step for circulation of hot air in the first circuit C1, in particular for preventing condensation in the first circuit C1, upstream from the filtration means 12.

The hot air circulation step in the first circuit C1 makes it possible to reach more quickly the target temperature values, in particular said target temperature (Tc).

Preferably, hot air circulation that has a temperature that is at least equal to said target temperature (Tc) is maintained for a specified period, for example about 10 minutes, through the first circuit C1 and the filtration means 12.

As indicated above, the heating of the air continues after the preheating step following a heating step consisting in continuously heating, at said target temperature (Tc), the air that is intended to be used for sterilization.

The heating means 36 that comprise said at least one heater are supplied electrically to obtain said hot air, and said heating means 56 of said at least one evaporator 46 are also supplied to obtain the hydrogen peroxide vapor.

The preliminary phase of the sterilization method also comprises steps for preparing the second circuit C2 of hydrogen peroxide ($H_2O_2$).

Preferably, the preliminary phase comprises at least one draining step that consists in purging all or part of the second circuit C2 and in particular the reservoir 76.

The draining step consists in at least controlling the opening of the regulating means 92 and 98 to purge the reservoir 76.

The opening of the regulating means 98 makes it possible for hydrogen peroxide to circulate through the purge pipe 96, from the reservoir 76 to the discharge means 97.

The opening of the regulating means 92 makes it possible to expose the reservoir 76 to the open air (at atmospheric pressure); the hydrogen peroxide that is optionally present in the second circuit C2 and most particularly in the bottom of the reservoir 76 is then likely to be discharged via the purge pipe 96.

Preferably, the draining step is interrupted after a specified length of time, for example a period of at least five seconds after there is no measurement (or loss of information) by the low-level measuring means 86, which, combined with the reservoir 76, are connected to the control unit.

The draining step comprises, in addition to a purge of the reservoir 76, a purge of the hydrogen peroxide supply pipe 78 of the second circuit C2.

The regulating means 84 are controlled in the open position to allow the flow of the hydrogen peroxide that is present in the supply pipe 78 toward the reservoir 76, the regulating means 98 then also being in the open position toward the discharge means 97.

The regulating means 92 and 98 are kept in the open position during the purging of the supply pipe 78.

Advantageously, the hydrogen peroxide that is present in the second circuit C2 is totally purged owing to the draining step so as to be able to ensure that the properties of the sterilizing agent are not altered.

Once the draining step is carried out, the filling of the reservoir 76 of the second circuit C2 is initiated with "fresh" hydrogen peroxide so that the second circuit C2 is operational to deliver said hydrogen peroxide in the liquid state.

The filling step as also the draining step are implemented during said preliminary phase in the sterilization of the filtration means 12.

The method comprises a filling step that consists in filling said at least one reservoir 76 with sterilizing agent that consists of hydrogen peroxide in the liquid state.

The reservoir 76 constitutes means for storing hydrogen peroxide whose capacity makes possible, preferably, the storage of a specified amount corresponding to the necessary amount to carry out a sterilization cycle of the filtration means 12.

To initiate filling, the closing of the regulating means 98 arranged in the purge pipe 96 is controlled.

In the embodiment of the sterilization device 10, the control unit regulates the solenoid valve that constitutes the regulating means 98 from their open position to their closed position.

The filling of the reservoir 76 is carried out from the hydrogen peroxide supply source 80 through the supply pipe 78.

During the filling, the regulating means 84 and 92 are in the open position, and the regulating means 74 are in the closed position.

The filling continues until the high-level measuring means 88, combined with the reservoir 76, detect hydrogen peroxide.

At the end of the filling step, the reservoir 76 contains at least the specified amount of liquid hydrogen peroxide for sterilizing said filtration means 12 according to the method.

The preliminary phase is then completed, and the sterilization phase itself of the filtration means 12 can begin.

In accordance with the invention, the sterilization method of the gas filtration means 12 comprises at least:
A preliminary phase that comprises:
A step for isolating filtration means 12, in particular in relation to the air blowing circuit that is located downstream from said filtration means to be sterilized;
A step for preheating the air that is used in the sterilization method that consists in heating the air that is delivered by the compressed-air supply source until reaching at least a specified target temperature Tc;
When the preliminary phase is completed, then a sterilization phase can begin;
The sterilization phase comprises:
An application step that consists in circulating through the gas filtration means 12 a gaseous mixture that comprises hot air and a specified amount of hydrogen peroxide vapor, in which said specified amount of hydrogen peroxide vapor is obtained by sequentially injecting, with a given time interval (t) between two successive injections, a given dose of hydrogen peroxide in the liquid state in the hot air; and
A sterilization step that consists, during said time interval (t), in maintaining the circulation of hot air through said filtration means to eliminate by evaporation all or part of the hydrogen peroxide that is deposited on said filtration means during said application step.

In this method for sterilizing the filtration means, the same hot air is used in the application step as in the sterilization step.

In other words, after having carried out the preliminary phase for the implementation of the filter sterilization method, said method comprises a continuous application of a stream of hot air that passes through at least one filter that is to be sterilized, a step for injection of a given dose of hydrogen peroxide into the stream of hot air for applying hydrogen peroxide to the filter; this application step is followed by a sterilization step that consist in allowing time to the stream of hot air to evaporate the hydrogen peroxide that is injected during the preceding step and being in the area of the filter; these two steps are repeated as many times as it is necessary so that the specified amount of hydrogen peroxide is reached for carrying out the sterilization cycle of the filtration means.

In accordance with the invention, the method for sterilizing gas filtration means 12 comprises at least:

An application step that consists in circulating, through the gas filtration means 12, a gaseous mixture that comprises hot air and a specified amount of hydrogen peroxide vapor, in which said specified amount of hydrogen peroxide vapor is obtained by sequentially injecting, with a given time interval (t) between two successive injections, a given dose of hydrogen peroxide in the liquid state in the hot air; and A sterilization step that consists, during at least said time interval (t), in circulating the hot air through said filtration means 12 to eliminate by evaporation all or part of the hydrogen peroxide that is deposited on said filtration means 12 during said application step.

The sterilization method consists in carrying out, first of all, a step for application of a gaseous mixture that contains hydrogen peroxide in the vapor state to the filtration means 12.

The application of the sterilization agent formed by the hydrogen peroxide is carried out by circulating, through the filtration means 12, a gaseous mixture that consists of hot air and a fraction of the specified amount of hydrogen peroxide vapor.

According to an important characteristic, the gaseous mixture comprises a fraction of the specified amount of hydrogen peroxide vapor that results from the sequential injection into the hot air of a given dose of hydrogen peroxide in the liquid state.

The injection of hydrogen peroxide in the liquid state is carried out sequentially with a given time interval (t) between two successive injections.

To obtain said gaseous mixture, the method comprises at least one step for vaporization of the hydrogen peroxide.

The vaporization step consists in vaporizing said given dose of hydrogen peroxide in the liquid state in evaporation means formed by the evaporator 46 to obtain said gaseous mixture that is used during the application step.

Advantageously, the vaporization is achieved by injecting said given dose of hydrogen peroxide in the liquid state into a continuous stream (or "vein") of hot air and then in introducing the entire dose into the evaporator 46 to obtain said gaseous mixture that is used during the application step.

With a sterilization device 10 according to the embodiment, the injection of said given dose of hydrogen peroxide during the vaporization step is achieved by selectively controlling the opening of the regulating means 74 during a given period of time.

The opening of the regulating means 74 during said given period of time makes it possible, for a specified flow rate of hydrogen peroxide in the injection pipe 52, to inject by means of the injection means 50 said given dose that is desired into the hot air that continuously circulates through the connection 48.

In the sterilization device 10, the sequential injection is achieved by selectively controlling the closing of said regulating means 74 during said given time interval (t) between two successive injections of a given dose of hydrogen peroxide in the liquid state.

By way of non-limiting example on a sequence of a total duration of 30 seconds, the regulating means 74 are controlled in the open position during a period of time of one second for injecting said given dose into hot air and then are controlled in the closed position during a time interval of 29 seconds.

During said time interval (t), no hydrogen peroxide is injected any longer via the injection means 50, and only the hot air that is delivered by the pipe 24 of the first circuit C1 continues to circulate, from the evaporator 46, through the pipe 60 and the filtration means 12.

It is at least during this time interval (t) that said sterilization step is carried out. Actually, the sterilization step consists in circulating the hot air through said filtration means 12 to eliminate by evaporation all or part of the hydrogen peroxide that was previously deposited during said application step.

Advantageously, the hydrogen peroxide is deposited by condensation on the filtration means 12 during said application step.

By comparison with a continuous injection, the sequential injection of a given dose of hydrogen peroxide makes it possible to deposit a fraction of the specified amount of hydrogen peroxide on the filtration means 12.

Said given dose of hydrogen peroxide is determined in particular in such a way as not to saturate or clog the filtration means 12.

Owing to the sequential injection, the fraction of said specified amount of hydrogen peroxide vapor that condenses in the filtration means 12 is likely to be activated thermally and evaporated by the hot air during said time interval (t).

In a filtration device 10, the given dose of hydrogen peroxide in the liquid state is introduced by the hot air into the cavity 54 of the evaporator 46 where the hydrogen peroxide is then vaporized by the heating means 56.

The gaseous mixture resulting therefrom consists of hot air and a fraction of the specified amount of hydrogen peroxide vapor, which is then routed by the pipe 60 to the filtration means 12 that are to be sterilized.

The regulating means 62 are in the open position, allowing said gaseous mixture to circulate from the evaporator 46 to the filtration means 12.

The part of the gaseous mixture that passes through said filtration means 12 is then discharged by means of the discharge pipe 64 in the direction of the collecting means 66, with the regulating means 68 being in the open position.

Based on the value of the time interval (t), the sterilization step that follows the application step makes it possible to eliminate all or part of the hydrogen peroxide condensates with hot air before initiating a new application step by injection of the following given dose.

When the value of the time interval (t) is too short to ensure in particular a complete elimination of the hydrogen peroxide, the sterilization method then advantageously comprises a so-called additional sterilization step that consists in circulating only the hot air through said filtration means 12 during a specified period (D).

The additional sterilization step is carried out once the application is completed, in the form of said successively-injected doses of the desired amount of hydrogen peroxide, which amount corresponds to, for example, the capacity of the reservoir 76.

By way of non-limiting example, the additional sterilization step consists in circulating through the filtration means 12 only hot air for a period D of between 15 to 40 minutes, preferably 25 minutes, to ensure complete evaporation of the hydrogen peroxide.

At least a part of the "chemical" sterilization of the filtration means 12 according to the method therefore is produced during the time interval (t) and can, if necessary, be completed during such an additional sterilization step.

When the gaseous mixture brought in via the pipe 60 comes into contact with the filtration means 12 whose temperature is lower, the hydrogen peroxide in the vapor state will then be deposited by condensation on the filtration means 12.

At the end of the application step, the filtration means 12 comprise at least on the surface hydrogen peroxide condensates that result from a change in state, from the vapor state to the liquid state, having taken place when the hydrogen peroxide vapor contained in the gaseous mixture comes into contact with said filtration means 12.

Once said given dose of hydrogen peroxide is injected and is vaporized in the evaporator 46, the pipe 24 continues to deliver hot air at the target temperature (Tc).

This hot air passes through the evaporator 46 and continues its path in the sterilization device 10 until coming into contact with the filtration means 12.

The hot air that comes into contact with the filtration means 12 then has, for example, a temperature of between 100° C. and 120° C., which will gradually bring about the evaporation of said hydrogen peroxide condensates.

The hot air thermally activates the hydrogen peroxide ($H_2O_2$) by acting on the chemical bonds of hydrogen peroxide; by breaking said bonds, the hot air brings about the appearance of very active free radicals (OH) that will destroy the microorganisms and make it possible to achieve the desired sterilization.

The hot air gradually evaporates the water that is present in the hydrogen peroxide condensates, which brings about an increase in the hydrogen peroxide concentration and in so doing increases the sterilizing effect.

Once evaporated, the hydrogen peroxide in the gaseous state easily passes through the filtration means 12 without altering the structure thereof.

Advantageously, the method comprises a treatment step that consists in treating the effluents that are obtained from the sterilization and most particularly the hydrogen peroxide in the gaseous state.

This is the reason for which the sterilization device 10 comprises treatment means 70 that are arranged in the discharge pipe 64, upstream from the collecting means 66.

A sterilization cycle according to the method consists in successively repeating the sequence that consists of said application and sterilization steps "n" number of times.

During a sequence of the sterilization cycle, the regulating means 74 are controlled by opening them for injecting said specified dose of hydrogen peroxide, in the example by means of injection means 50.

The application step is then carried out as was described above.

The regulating means 74 are then controlled by closing them during the time interval (t) so as to carry out the sterilization step.

According to the examples of values indicated above, for a sequence of a total duration of 30 seconds, the regulating means 74 are open for a second and then closed for 29 seconds.

When the time interval (t) is relatively short as in the example above, an additional sterilization step is then carried out, for example for a duration D of between 15 to 40 minutes, preferably 25 minutes.

As will become clear, said additional sterilization step is, however, optional and could advantageously be eliminated by increasing said time interval (t), for example to approximately five minutes between each hydrogen peroxide injection.

Advantageously, the sequence of said application and sterilization steps is repeated "n" number of times, for example between five and 25 times according to the applications.

The repetition of the sequence is independent of the value of the time interval (t) and the implementation of said additional sterilization step.

Preferably, the capacity of the reservoir 76 corresponds to the specified amount of hydrogen peroxide that is necessary to the repetition of the sequence, or at least to "n" times said given dose of hydrogen peroxide that is injected sequentially.

For a sterilization cycle, only a single filling step is then carried out initially during the preliminary preparation phase of the sterilization device 10.

As explained above, the alternating repetition of said steps for applying a fraction of the specified amount of hydrogen peroxide vapor that is obtained from said given dose and hot air advantageously makes it possible not to saturate the filtration means 12.

For an equal amount of hydrogen peroxide vapor, the sterilization of the filtration means 12 that is obtained is thus better accomplished by successively carrying out the sequence that is formed by said application and sterilization steps "n" times than by projecting an equivalent amount of hydrogen peroxide vapor a single time.

With the sequential injection according to the sterilization method of the invention, the elimination of hydrogen peroxide by evaporation by means of hot air requires by comparison less energy than would be necessary to obtain the evaporation of an equivalent amount that would be injected only one time.

To evaporate an equivalent amount of hydrogen peroxide that is not injected sequentially but only one time, it would actually be necessary to increase the temperature of the hot air that would have the consequence of increasing the necessary energy, or it would also be necessary to increase the flow rate of the hot air.

However, such an increase of the temperature and/or the flow rate of hot air that is used in the sterilization method would have the consequence of running the risk of deteriorating the filtration means 12, as was the case previously with water vapor.

Advantageously, the sterilization method according to the invention therefore does not make it possible only to sterilize the filtration means 12 effectively but also not to deteriorate them to make possible again the use after the sterilization.

By preserving the filtration means 12, the sterilization method according to the invention advantageously makes it possible to increase its service life, which contributes to reducing the costs.

The method and the device for sterilization of gas filtration means are designed in particular to be used for the sterilization of blowing-air filtration means in an installation for manufacturing containers made of thermoplastic material from hot preforms.

The invention claimed is:

1. A method for sterilizing gas filtration means, the method comprising:
   heating a stream of compressed air to about 220° C. to obtain a continuous stream of hot air;
   delivering the heated air to a chamber, the chamber comprising a heating means;
   injecting sequentially, with a given interval (t) of time between two successive injections, a given dose of hydrogen peroxide in the liquid state introduced into the continuous stream of the hot air to form a gaseous mixture comprising hot air and the hydrogen peroxide;
   applying, by circulating the gaseous mixture through the gas filtration means a specified amount of hydrogen peroxide vapor, in which said specified amount of hydrogen peroxide is a total amount necessary to sterilize the gas filtration means for a sterilization cycle and wherein the given dose is a fraction of the specified amount; and
   sterilizing by circulating the continuous stream of hot air through said filtration means during said interval (t) to eliminate by evaporation all or part of the hydrogen peroxide that is deposited on said filtration means during said applying step.

2. The sterilization method according to claim 1, further comprising:
   vaporizing said given dose of hydrogen peroxide in the liquid state in evaporation means to obtain said gaseous mixture that is used during the applying step.

3. The sterilization method according to claim 2, wherein the injecting of said given hydrogen peroxide dose is carried out sequentially by selectively controlling regulating means, respectively in the open position during a given period of time and in the closed position during the given time interval (t) between two successive injections of said given dose of hydrogen peroxide in the liquid state.

4. The sterilization method according to claim 1, wherein the applying and sterilizing steps are repeated "n" number of times per cycle.

5. The sterilization method according to claim 4, further comprising:
   sterilizing, in a second operation, by circulating only hot air through said filtration means for a period (D) that is specified based on the time interval (t) to ensure evaporation of hydrogen peroxide.

6. The sterilization method according to claim 2, wherein the applying and sterilizing steps are repeated "n" number of times per cycle.

7. The sterilization method according to claim 3, wherein the applying and sterilizing steps are repeated "n" number of times per cycle.

* * * * *